US 11,311,179 B2

(12) United States Patent
Koyama

(10) Patent No.: US 11,311,179 B2
(45) Date of Patent: Apr. 26, 2022

(54) ENDOSCOPE

(71) Applicant: OLYMPUS CORPORATION, Tokyo (JP)

(72) Inventor: Reiji Koyama, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/899,783

(22) Filed: Jun. 12, 2020

(65) Prior Publication Data

US 2020/0305686 A1    Oct. 1, 2020

Related U.S. Application Data

(60) Division of application No. 15/610,879, filed on Jun. 1, 2017, now abandoned, which is a continuation of (Continued)

(30) Foreign Application Priority Data

Dec. 3, 2014   (JP) ................................. 2014-245197

(51) Int. Cl.
*A61B 1/005*   (2006.01)
*A61B 1/00*    (2006.01)
*G02B 23/24*   (2006.01)

(52) U.S. Cl.
CPC .............. *A61B 1/0052* (2013.01); *A61B 1/00* (2013.01); *A61B 1/0057* (2013.01); *G02B 23/24* (2013.01)

(58) Field of Classification Search
CPC ....... A61B 1/0052; A61B 1/00; A61B 1/0057; A61B 1/0016; A61B 1/0008; A61B 1/0011; G02B 23/24
See application file for complete search history.

(56) References Cited

U.S. PATENT DOCUMENTS 4,557,254 A    12/1985  Yamaguchi
5,507,717 A *   4/1996  Kura ................... A61B 1/0052
                                                     600/146

(Continued)

FOREIGN PATENT DOCUMENTS

JP   H03-049682 Y   10/1991
JP   2000-051148 A   2/2000
(Continued)

OTHER PUBLICATIONS

International Search Report dated Jan. 26, 2016 issued in PCT/JP2015/081144.

(Continued)

*Primary Examiner* — Timothy J Neal
*Assistant Examiner* — Genja M Frankert
(74) *Attorney, Agent, or Firm* — Scully, Scott, Murphy & Presser, P.C.

(57) ABSTRACT

An endoscope including: a bending portion; a first traction member and a second traction member that causes the bending portion to bend; a first rotary member that pulls the first traction member; a first plate member on which the first rotary member and the first traction member are disposed; a first protrusion; a first positioning part that comes into contact with the first rotary member; a second rotary member that pulls the second traction member; a second plate member; a second protrusion; and a second positioning part that comes into contact with the second rotary member.

3 Claims, 12 Drawing Sheets

Related U.S. Application Data application No. PCT/JP2015/081144, filed on Nov. 5, 2015.

(56) References Cited

U.S. PATENT DOCUMENTS

| | | | |
|---|---|---|---|
| 6,236,876 B1* | 5/2001 | Gruner | A61B 1/0052 600/114 |
| 2004/0049097 A1* | 3/2004 | Miyake | G02B 23/2476 600/150 |
| 2004/0054259 A1 | 3/2004 | Hasegawa et al. | |
| 2005/0054899 A1* | 3/2005 | Miyake | A61B 1/0057 600/152 |
| 2006/0069311 A1 | 3/2006 | Sullivan et al. | |
| 2008/0051631 A1 | 2/2008 | Dejima et al. | |
| 2008/0086031 A1 | 4/2008 | Mitsuya | |
| 2008/0200763 A1 | 8/2008 | Ueno | |
| 2008/0249365 A1 | 10/2008 | Masaki | |
| 2008/0262306 A1 | 10/2008 | Kawai | |
| 2008/0262310 A1 | 10/2008 | Kawai | |
| 2009/0292169 A1 | 11/2009 | Mitani et al. | |
| 2012/0078054 A1 | 3/2012 | Ueno et al. | |
| 2012/0302949 A1 | 11/2012 | Takemoto | |
| 2013/0079711 A1 | 3/2013 | Nair et al. | |
| 2013/0102960 A1 | 4/2013 | Miyoshi | |
| 2013/0190567 A1 | 7/2013 | Miyoshi et al. | |
| 2014/0088497 A1* | 3/2014 | Campbell | A61B 1/0052 604/95.04 |
| 2015/0351610 A1* | 12/2015 | Fan | A61B 1/0057 600/148 |

FOREIGN PATENT DOCUMENTS

| | | |
|---|---|---|
| JP | 2001-046329 A | 2/2001 |
| JP | 2013-223735 A | 10/2013 |

OTHER PUBLICATIONS

Office Action dated Feb. 14, 2020 received in U.S. Appl. No. 15/610,879.

* cited by examiner

ENDOSCOPE

CROSS REFERENCE TO RELATED APPLICATION

This application is a divisional application of U.S. patent application Ser. No. 15/610,879 filed on Jun. 1, 2017, which is a continuation application of PCT/JP2015/081144 filed on Nov. 5, 2015 and claims benefit of Japanese Application No. 2014-245197 filed in Japan on Dec. 3, 2014, the entire contents of each of which are incorporated herein by reference.

BACKGROUND OF INVENTION

1. Field of the Invention

The present invention relates to an endoscope in which a traction member is pulled along with rotation of a rotatable member to bend a bending portion provided in an insertion section.

2. Description of the Related Art

An endoscope is used in a medical field, an industrial field, and other fields. The endoscope has a rigid elongated insertion section or a flexible elongated insertion section. Typically, the endoscope having a flexible insertion section is provided with a bending portion at distal end side of the insertion section. The bending portion is configured by connecting a plurality of bending pieces to one another.

The bending portion is typically configured to be bent in response to pulling and relaxing of a bending wire that is operated by a bending operation device provided in an operation section. A distal end of the bending wire is fixed to a predetermined position of a distal end bending piece that constitutes the bending portion.

The endoscope including the bending portion makes it possible to direct an observation optical system provided in a distal end portion of the insertion section, toward a desired direction to allow for observation, and to smoothly insert the insertion section to a deep portion, by bending the bending portion.

In an endoscope disclosed in Japanese Patent Application Laid-Open Publication No. 2013-223735, the bending wire is pulled and relaxed through rotation of a pulley along with operation of the bending operation device. The pulley is a bending operation mechanism inside the operation section. A proximal end of the bending wire is fixed to, for example, a spherical body by solder, and the spherical body to which the wire has been fixed is installed in a spherical hole provided in the pulley. As a result, as illustrated in FIG. 4 of Japanese Patent Application Laid-Open Publication No. 2013-223735, a bending wire 12 is wound and disposed in each of a peripheral groove of one pulley 11UD and a peripheral groove of the other pulley 11LR.

Further, the one pulley 11UD wound with the bending wire 12 and the other pulley 11LR wound with the bending wire 12 are disposed in a pulley housing concave section. The pulley housing concave section has a substantially semi-annular wall surface that prevents the wire from being detached.

In contrast, in a method of eliminating slack of an operation wire of an endoscope in Japanese Patent Application Laid-Open Publication No. 2000-051148, a sprocket serving as a bending operation mechanism in an operation section is rotated to move a chain along with operation of a bending operation device, which causes a bending wire to be pulled and relaxed. As illustrated in FIG. 3 to FIG. 5 of Japanese Patent Application Laid-Open Publication No. 2000-051148, proximal ends of respective operation wires 39 of an endoscope 20 are respectively attached to, through a coupling member 38, an end part of a UD chain member 29B and an end part of an LR chain member 29A. The UD chain member 29B is wound around a UD sprocket 28B, and the LR chain member 29A is wound around an LR sprocket 29.

The UD sprocket 28B with which the UD chain member 29B engages and the LR sprocket 28A with which the LR chain member 29A engages are restricted in position on an insertion section 2 side by a pressing part 30 that is formed integrally with a partition plate 25. In addition, the chain members 29A and 29B respectively engaging with the UD sprocket 28B and the LR sprocket 28A are prevented from being detached from the sprockets 28A and 28B by a cover member 33 that is fixed to a ground plate 24 by screwing.

SUMMARY OF THE INVENTION

An endoscope according to one aspect of the present invention includes: a bendable bending portion provided in an insertion section that is inserted into a subject; a first traction member and a second traction member that are pulled to bend the bending portion; a first rotary member including a first engaging part that engages with the first traction member, a first shaft part that fixes the first engaging part, and a first insertion hole that penetrates in an axial direction of the first shaft part, the first rotary member causing the first traction member to engage with the first engaging part to wind the first traction member, and rotating to pull the first traction member; a first plate member on which the first rotary member and the first traction member are disposed, the first plate member being formed in a plate shape; a first protrusion protruding from the first plate member to position the first rotary member and the first traction member with respect to the first plate member; a first positioning part protruding from the first plate member to position the first rotary member, and coming into contact with the first shaft part of the first rotary member; a second rotary member including a second engaging part that engages with the second traction member, a second shaft part that fixes the second engaging part, and a second insertion hole that penetrates in an axial direction of the second shaft part, the second rotary member causing the second traction member to engage with the second engaging part to wind the second traction member, and rotating to pull the second traction member; a second plate member that is a plate member including a first surface disposed on an end surface of the first protrusion and a second surface on which the second rotary member and the second traction member are disposed, the second surface being a rear surface side of the first surface, the second plate member including a third insertion hole that penetrates the first surface and second surface and is disposed so as to be coaxial with the first insertion hole; a second protrusion protruding from the second plate member to position the second rotary member and the second traction member with respect to the second plate member; and a second positioning part protruding from the second plate member to position the second insertion hole so as to be coaxial with the third insertion hole, the second positioning part coming into contact with the second shaft part of the second rotary member.

An endoscope according to one aspect of the present invention includes: a bendable bending portion provided in an insertion section that is inserted into a subject; a traction member pulled to bend the bending portion; a rotary member that includes an engaging part that engages with the traction member and a shaft part that fixes the engaging part, the rotary member causing the traction member to engage with the engaging part to wind the traction member and rotating to pull the traction member; a member on which the rotary member and the traction member are disposed, the member being formed in a plate shape; a protrusion protruding from the member to position the rotary member and the traction member with respect to the member; and a cutout part provided on the protrusion of the member and having a width set to cause a tip of thumb and a tip of fingers of an assembling worker of the endoscope, the thumb and the finger holding the rotary member and the traction member, to be located inside a predetermined installation space so that the assembling worker of the endoscope can perform positioning of the rotary member and the traction member with respect to the member in the predetermined installation space inside the protrusion while holding the rotary member and the traction member with the thumb and the finger.

An endoscope according to one aspect of the present invention includes: a bendable bending portion provided in an insertion section that is inserted into a subject; a traction member pulled to bend the bending portion; a pair of rotary members each including an engaging part that engages with the traction member and a shaft part that fixes the engaging part, the pair of rotary members each causing the traction member to engage with the engaging part to wind the traction member and rotating to pull the traction member; a member on which the pair of rotary members and the traction member are disposed, the member being formed in a plate shape; a protrusion protruding from the member to position each of the pair of rotary members and the traction member with respect to the member; and a pair of positioning parts each protruding from the member to position the pair of rotary members, and coming into contact with the shaft part of each of the pair of rotary members.

DETAILED DESCRIPTION OF THE PREFERRED EMBODIMENT(S)

Figure 1:
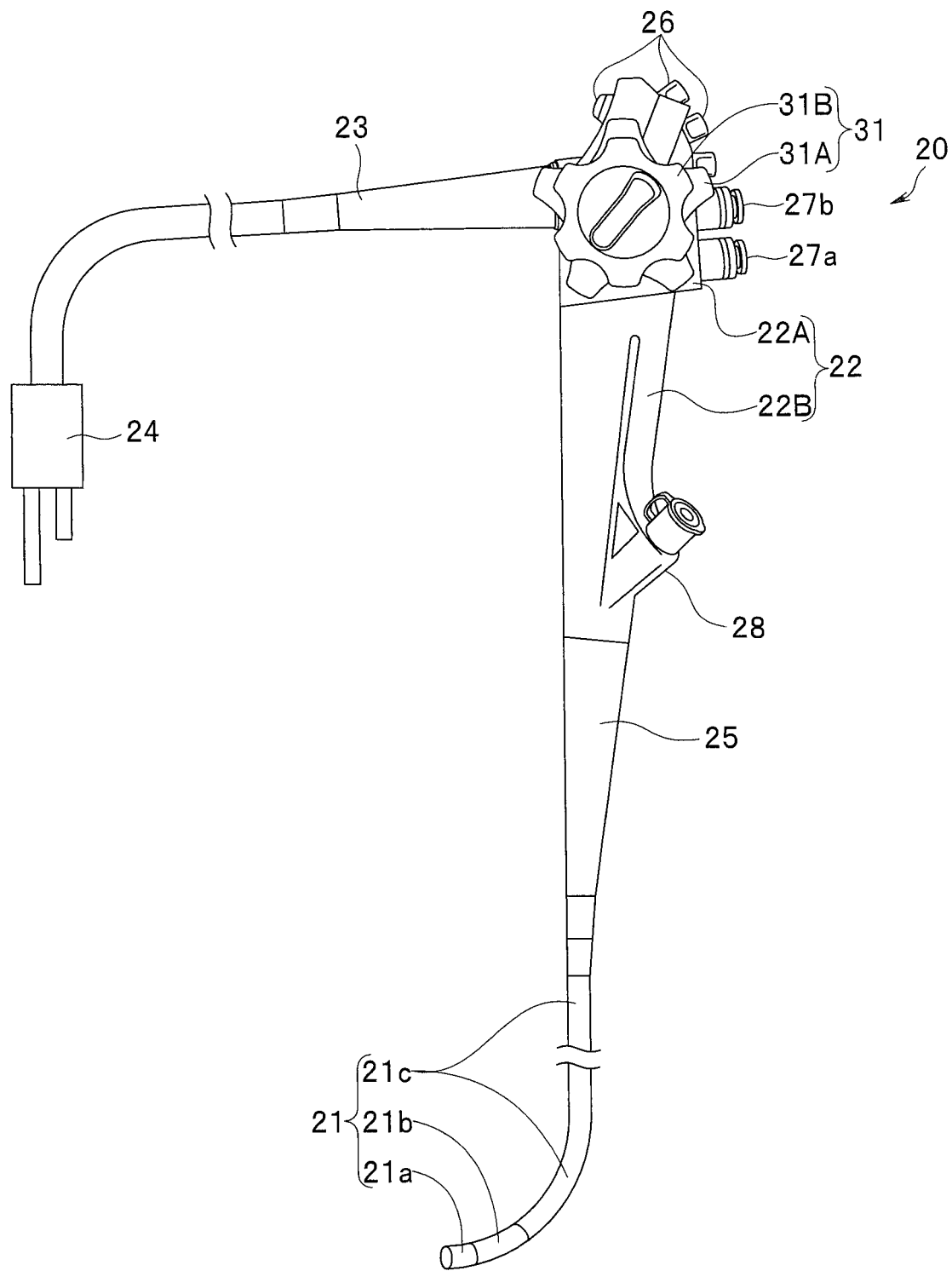
FIG. 1 is a side view of an endoscope, illustrating a side surface on a bending operation device side.

The present invention is described below with an illustrated embodiment.

In drawings used in the following description, scale sizes of some components are varied in illustration for each component in order to illustrate the components with respective recognizable sizes in the drawings. Therefore, the present invention is not limited to the number of components, shapes of the respective components, a size ratio of the components, and relative positional relationship between the components that are illustrated in the respective drawings.

An outline of an entire configuration of an endoscope according to the present invention is described with reference to FIG. 1 and FIG. 2.

Figure 2:
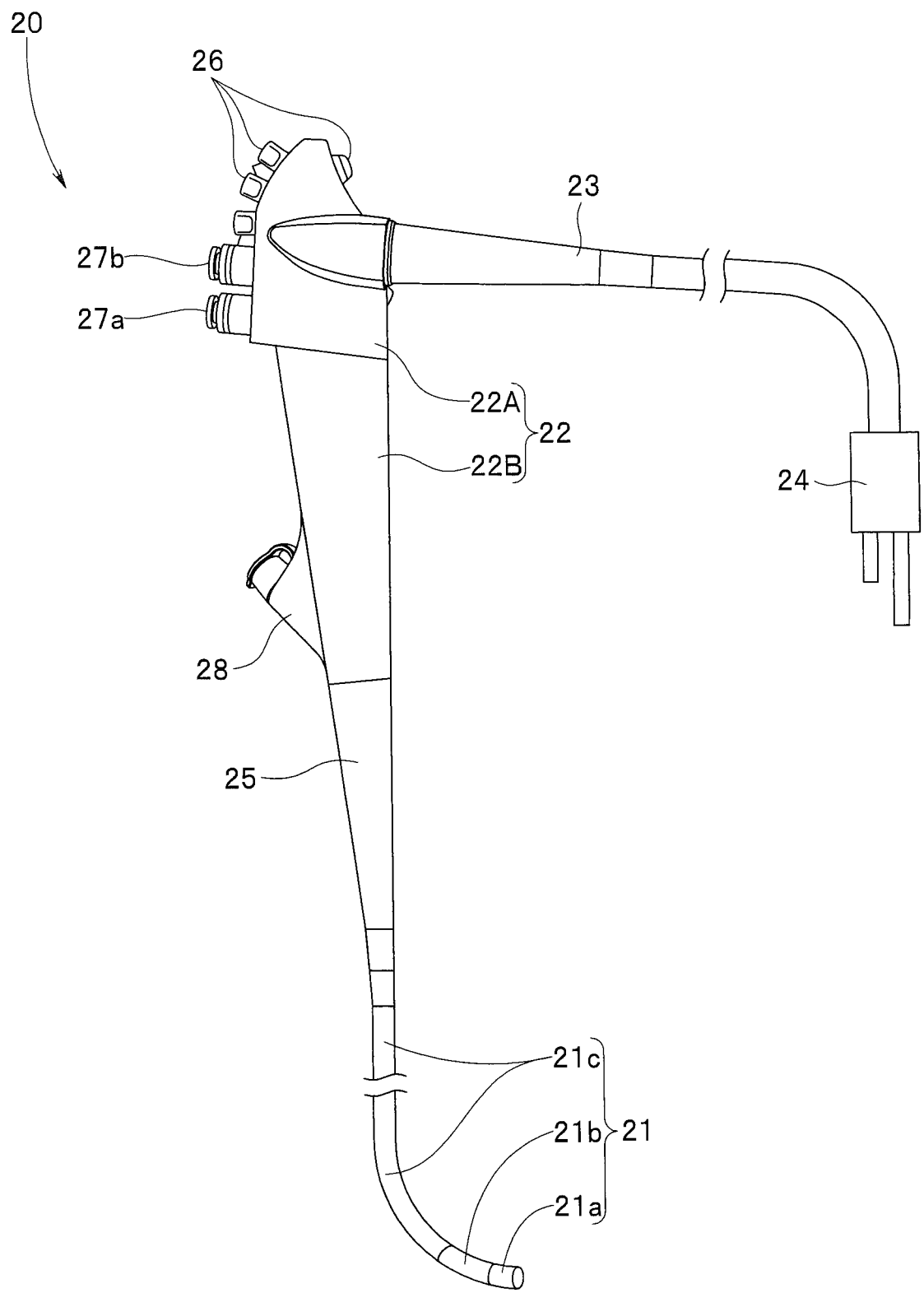
FIG. 2 is another side view of the endoscope, illustrating a side surface on a side opposite to the bending operation device side.

As illustrated in FIG. 1 and FIG. 2, an endoscope 20 mainly includes an elongated insertion section 21, an operation section 22, a universal cord 23, a connector 24, and other components. The insertion section 21 is inserted into a subject such as an inside of a body cavity. The operation section 22 is provided continuously to proximal end side of the insertion section 21. The universal cord 23 is extended from one side surface of the operation section 22. The connector 24 is provided at an end part of the universal cord 23.

The insertion section 21 includes a rigid distal end component 21a, a bending portion 21b bendable in four directions, and an elongated flexible tube portion 21c that are coupled to one another in order from distal end side of the insertion section 21. The bending portion 21b is bendable in four directions of upward, downward, rightward, and leftward, and in optional directions through combination of bending operation in the four directions.

Note that, as an internal configuration unit for the bending operation of the bending portion 21b, a bending operation mechanism 30 is provided in the operation section 22. The detailed configuration of the bending operation mechanism 30 is described later.

Although illustration is omitted, an objective lens, an illumination lens, a cleaning nozzle, and a treatment instrument channel opening are provided on a distal end surface of the distal end component 21a.

Although illustration is omitted, an air feeding conduit and a water feeding conduit that are coupled to the cleaning nozzle, a light guide fiber that supplies illumination light to the illumination lens, and the like are provided inside the distal end component 21a, in addition to an image pickup device, an electric substrate mounted with electric parts, a video cable extended from the image pickup device, and the like.

The video cable and the light guide fiber pass through the inside of the insertion section 21, the operation section 22, and the universal cord 23, and are extended to the connector 24. In addition, the air feeding conduit and the water feeding conduit pass through the insertion section 21 and are extended to the connector 24 through an air/water feeding cylinder and the universal cord 23 that are provided in the operation section 22.

The operation section 22 includes an operation section body 22A and a grasping portion case body 22B that are integrally and water-tightly fixed to each other. A proximal end portion of the insertion section 21 is provided continuously with an end part of the grasping portion case body 22B.

A reference numeral 25 denotes a bend preventing portion. The bend preventing portion 25 prevents buckling of the flexible tube portion 21c of the insertion section 21. The bend preventing portion 25 includes an elastic rubber member or the like, and covers a coupling portion between the end part of the grasping portion case body 22B and the proximal end portion of the insertion section 21.

Various kinds of operation members, for example, a plurality of electric switches 26, an air/water feeding button 27a, and a suction button 27b are provided on the operation section body 22A of the operation section 22. The electric switches 26 are provided for remote control of peripheral apparatuses such as a video processor. In addition, a vertical bending operation knob 31A and a lateral bending operation knob 31B of a bending operation device 31 are rotatably installed in the operation section body 22A. The bending operation device 31 is provided for the bending operation of the bending portion 21b of the insertion section 21.

A reference numeral 22Ac denotes an operation section body cover. The operation section body cover 22Ac is so fixed as to integrally and water-tightly block an opening (see a reference numeral 22Am in FIG. 5J) provided in the operation section body 22A. A reference numeral 28 denotes a treatment instrument guide opening that is provided in the grasping portion case body 22B.

Figure 3:
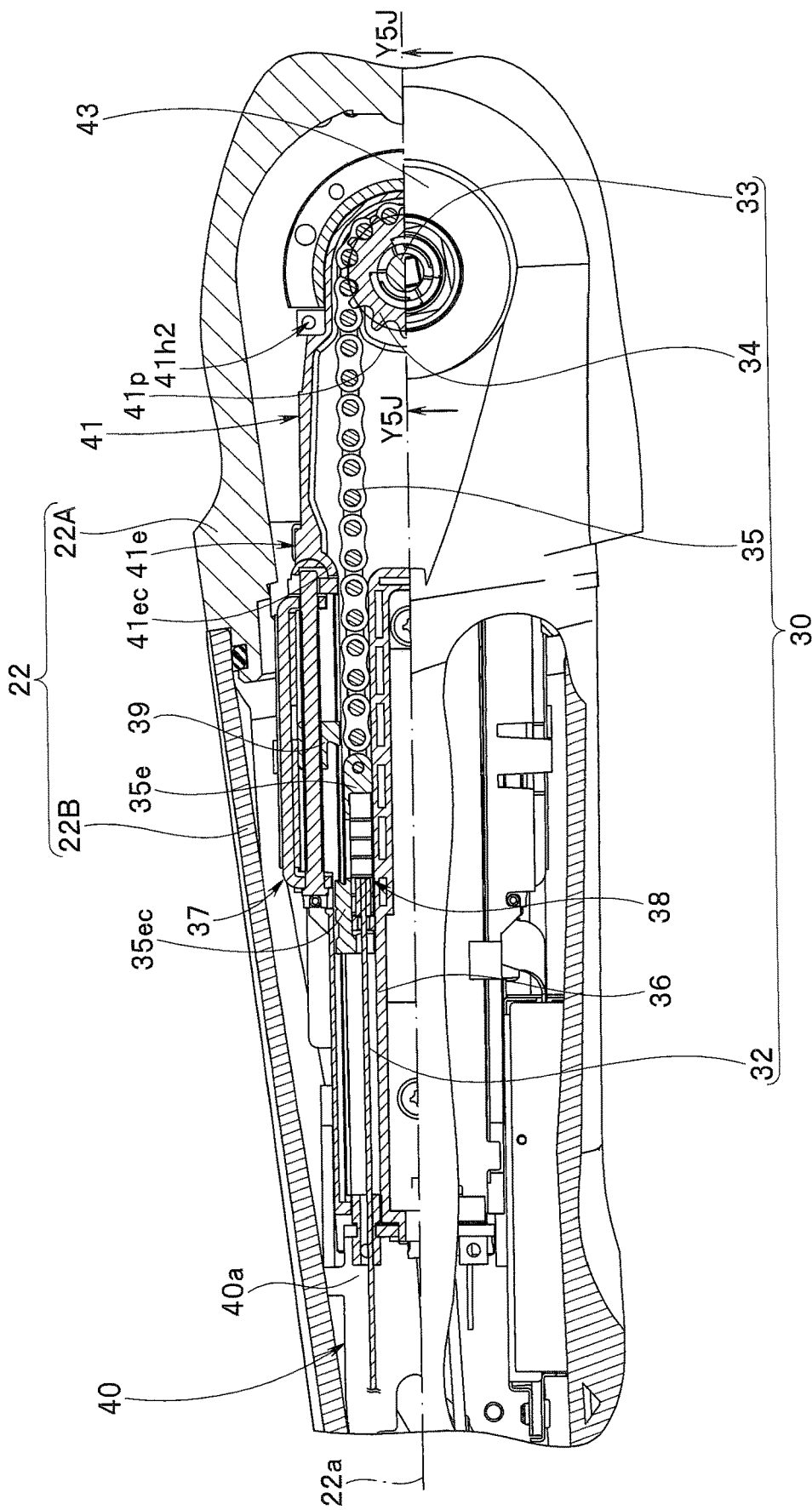
FIG. 3 is a diagram to explain a configuration inside an operation section and to explain a bending operation mechanism disposed on flat surface side of a main frame.

As illustrated in FIG. 3, a main frame 40 as a ground plate is installed inside the operation section 22. The main frame 40 is a first plate member out of members formed in a plate shape, and is fixed to an inside of the operation section body 22A of the operation section 22 and to an inside of the grasping portion case body 22B by screwing.

The bending operation mechanism 30, a partition 36, a bending adjustment unit 37, a chain cover 41, a lid member (see a reference numeral 42 in FIG. 4), a frame shaft 43, and the like are provided on flat surface 40a side of the main frame 40. The bending operation mechanism 30 moves bending wires 32 provided inside the insertion section 21, thereby bending the bending portion 21b.

The bending operation mechanism 30 mainly includes the bending operation device 31 illustrated in FIG. 1, the bending wires 32 and chains 35 that are traction members illustrated in FIG. 3, sprockets 34 serving as rotary members, and a support shaft 33.

In the present embodiment, the bending operation mechanism 30 includes a vertical bending operation mechanism and a lateral bending operation mechanism. The vertical bending operation mechanism may bend the bending portion 21b in a vertical direction. The lateral bending operation mechanism may bend the bending portion 21b in a lateral direction.

Figure 4:
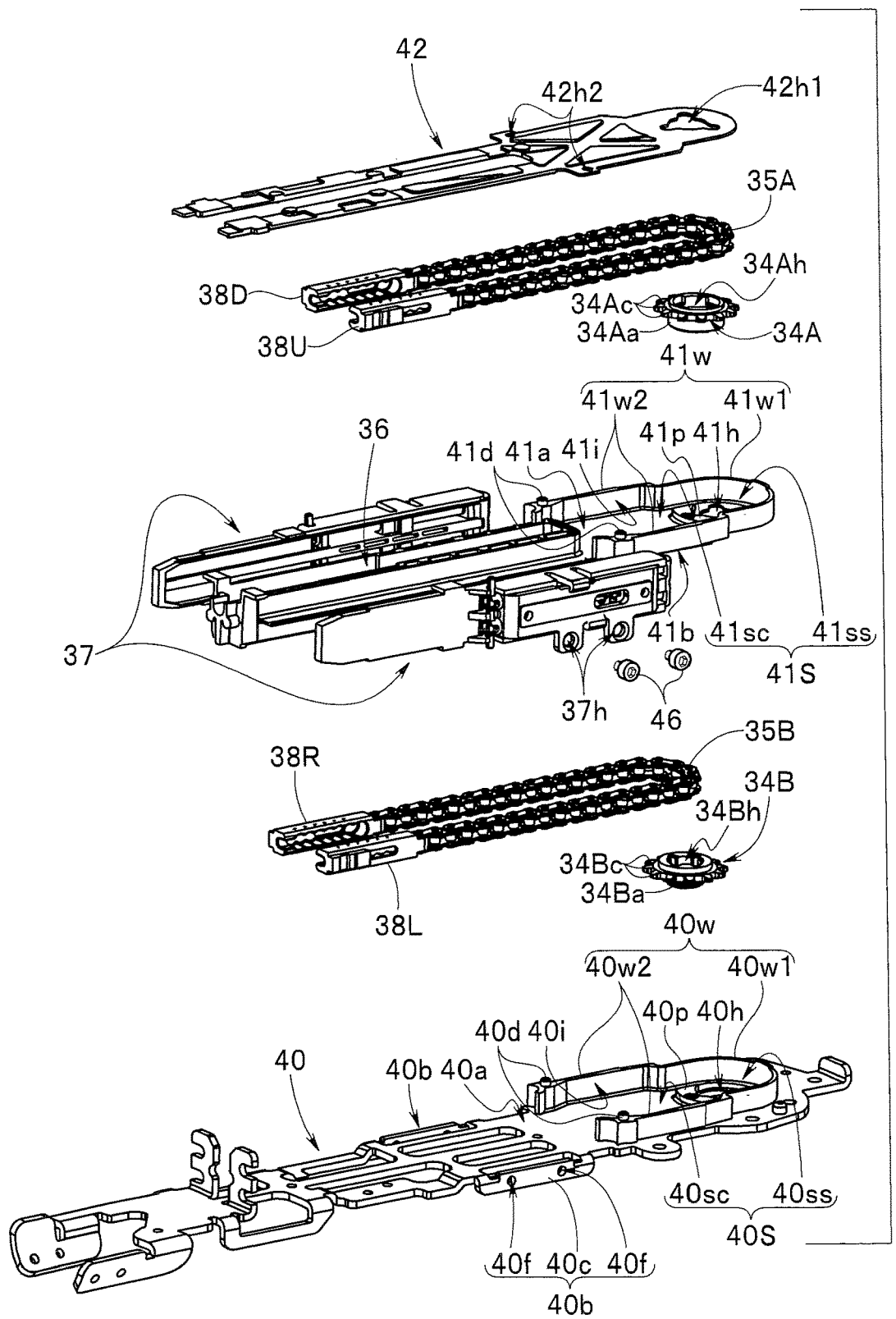
FIG. 4 is an exploded perspective view to explain the bending operation mechanism and other components.

Accordingly, as illustrated in FIG. 4, the bending operation mechanism 30 includes a vertical sprocket 34A and a lateral sprocket 34B as the sprocket 34, and a vertical chain 35A and a lateral chain 35B as the chain 35.

A reference numeral 34Aa denotes a vertical shaft part fixing a tooth part 34Ac, and a reference numeral 34Ba denotes a lateral shaft part fixing a tooth part 34Bc.

The vertical sprocket 34A rotates around the shaft along with rotating operation of the vertical bending operation knob 31A, and the lateral sprocket 34B rotates around the shaft along with the rotating operation of the lateral bending operation knob 31B. The vertical chain 35A engages with the tooth part 34Ac serving as an engaging part of the vertical sprocket 34A and is wound around the vertical sprocket 34A, and the lateral chain 35B engages with the tooth part 34Bc serving as an engaging part of the lateral sprocket 34B and is wound around the lateral sprocket 34B.

The chains 35A and 35B are moved respectively following the rotation of the sprockets 34A and 34B.

A reference numeral 38 in FIG. 3 denotes a known coupling member that couples the bending wires 32 to the corresponding chains 35. More specifically, a reference numeral 38U in FIG. 4 denotes an upper coupling member, a reference numeral 38D denotes a lower coupling member, a reference numeral 38L denotes a left coupling member, and a reference numeral 38R denotes a right coupling member.

The upper coupling member 38U couples an upper bending wire (not illustrated) to an end part of the vertical chain 35A. The lower coupling member 38D couples a lower bending wire (not illustrated) to the other end part of the vertical chain 35A. The left coupling member 38L couples a left bending wire (not illustrated) to an end part of the lateral chain 35B. The right coupling member 38R couples a right bending wire (not illustrated) to the other end part of the lateral chain 35B.

Note that the bending wires 32 that are respectively coupled to the chains 35A and 35B are moved along with rotating operation of the vertical bending operation knob 31A and rotating operation of the lateral bending operation knob 31B. Distal ends of the respective bending wires 32 are fixed to respective predetermined positions of distal end bending pieces (not illustrated) that constitute the bending portion 21b.

As illustrated in FIG. 3, a chain end portion configuring member 35e is provided at an end part of the chain 35. A reference numeral 39 denotes a stopper portion, and a contact part 35e of the chain end portion configuring member 35e projected toward outside comes into contact with the stopper portion 39, thereby regulating movement of the chain 35.

The main frame 40 illustrated in FIG. 4 has an elongated shape, and is formed through, for example, die casting. A support shaft hole 40h, a first chain housing wall 40w, and a first positioning projection 40p are provided at respective predetermined positions on the flat surface 40a of the main frame 40.

A reference numeral 40b denotes a unit fixing portion. Paired unit fixing portions 40b are so provided respectively on side parts of the main frame 40 as to face each other. Each of the unit fixing portions 40b includes an attachment part 40c and fixing parts, for example, two female screws 40f.

The bending adjustment unit 37 is integrally fixed to the attachment part 40c of the main frame 40. Male screws 46 are respectively inserted into unit attachment holes 37h and are respectively screwed with the female screws 40f to attach the bending adjustment unit 37.

The support shaft hole 40h is a through hole into which the support shaft 33 is inserted, and a center axis (not illustrated) of the support shaft hole 40h is orthogonal to a longitudinal axis (not illustrated) of the main frame. The first chain housing wall 40w and the first positioning projection 40p are provided at respective predetermined positions with respect to the support shaft hole 40h.

The first positioning projection 40p is a first pressing part serving as a positioning part that projects from the flat surface 40a by a predetermined amount. In contrast, the first chain housing wall 40w is a first protrusion part serving as a protrusion that integrally protrudes from the flat surface 40a by a predetermined amount. The first chain housing wall 40w includes a first annular wall 40w1 and a pair of first opposing walls 40w2.

A reference numeral 40S denotes a first bending operation mechanism housing chamber that includes the flat surface 40a and a first inner wall surface 40i of the first chain housing wall 40w that stands on the flat surface 40a. The lateral sprocket 34B wound with the lateral chain 35B is disposed inside the first bending operation mechanism housing chamber 40S.

The first annular wall 40w1 of the first chain housing wall 40w is a semicircular protrusion part, and the first opposing walls 40w2 are substantially straight parallel walls that are respectively extended from end parts of the first annular wall 40w1, in parallel to the longitudinal axis of the main frame.

The first annular wall 40w1 mainly constitutes a first sprocket installation space 40ss, prevents the lateral chain 35B wound around the lateral sprocket 34B from dropping off to the outside of the sprocket, and improves assemblability of the bending operation mechanism.

The first inner wall surface 40i of the first annular wall 40w1 is an inner peripheral surface of a predetermined radius, and a center of the inner peripheral surface is concentric with an axial center of the support shaft hole 40h.

The pair of first opposing walls 40w2 prevents the lateral chain 35B extended from the lateral sprocket 34B, from dropping off to the outside. A space between the first opposing walls 40w2 is a first chain installation space 40sc that absorbs slack of the lateral chain 35B in bending operation.

A reference numeral 40d denotes a first attachment dowel. The first attachment dowel 40d is provided at a predetermined position on end part side of each of the first opposing walls 40w2 and projects from a top surface of the end part by a predetermined amount.

The first positioning projection 40p retains the lateral sprocket 34B wound with the lateral chain 35B within the first annular wall 40w1, in other words, prevents displacement of the lateral sprocket 34B from the first sprocket installation space 40ss toward the first chain installation space 40sc.

Figure 5A:
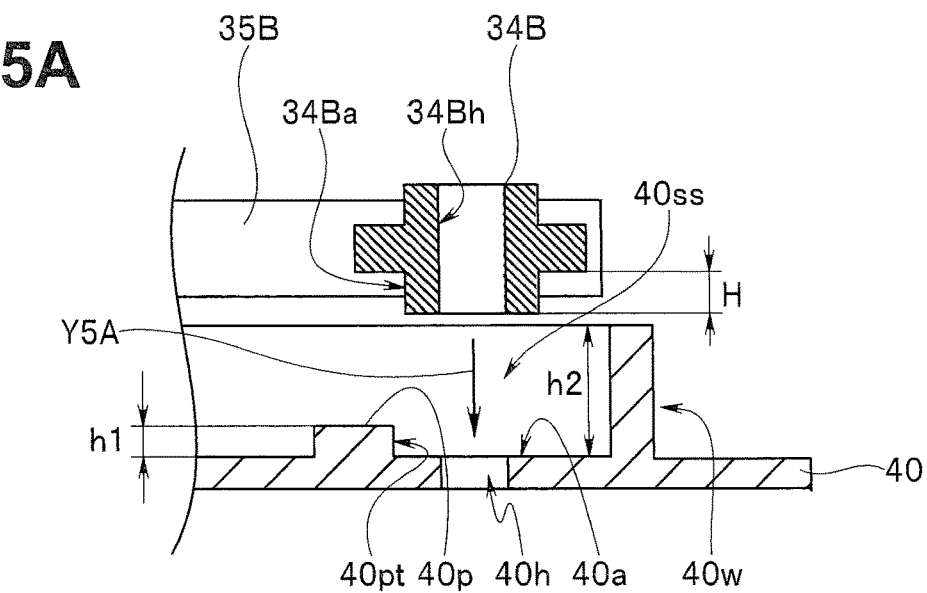
FIG. 5A is a diagram to explain relationship between the main frame and a lateral sprocket wound with a lateral chain.

A reference numeral 40pt illustrated in FIG. 5A denotes a first contact surface that comes into contact with the lateral shaft part 34Ba serving as a contact part of the lateral sprocket 34B. The first positioning projection 40p has a height h1 that is previously set lower than a protrusion height H of the lateral shaft part 34Ba.

In addition, the first chain housing wall 40w has a height h2 that is set larger by a predetermined amount than a length of the lateral sprocket 34B in the axial direction.

Figure 5B:
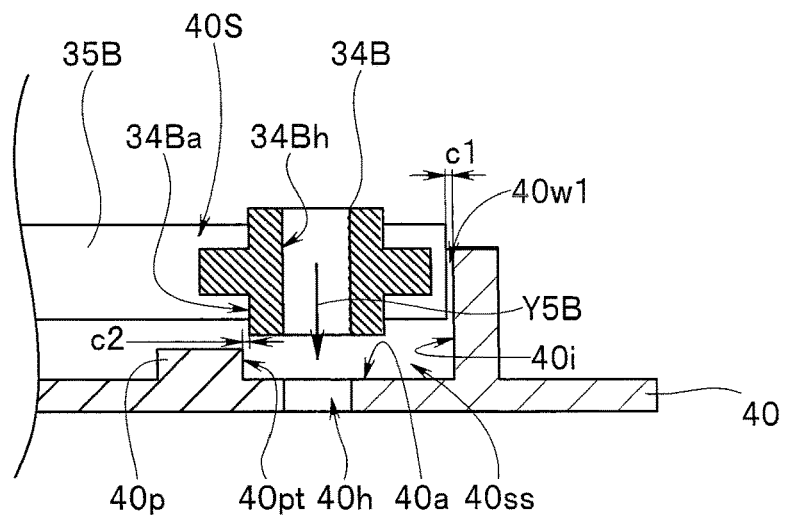
FIG. 5B is a diagram illustrating a state in which the lateral sprocket wound with the lateral chain is moved to a vicinity of a first positioning projection inside a first sprocket installation space of the main frame.

As illustrated in FIG. 5B, setting is performed such that a predetermined gap c1 is provided between the first inner wall surface 40i of the first annular wall 40w1 and the outer side of the lateral chain 35B wound around the lateral sprocket 34B.

In addition, the setting is performed such that a predetermined gap c2 is provided between the contact surface 40pt of the first positioning projection 40p and an outer peripheral surface of the lateral shaft part 34Ba.

Note that a distance from the axial center of the support shaft hole 40h to the contact surface 40pt is substantially equivalent to a sum of the radius of the lateral shaft part 34Ba and the gap c2.

The chain cover 41 illustrated in FIG. 4 is a second plate member out of the members formed in a plate shape, and includes a flat surface 41a and the other flat surface 41b that is a surface opposite to the flat surface 41a. The other flat surface 41b is a flat surface disposed to face the flat surface 40a of the main frame 40, and is disposed on an end surface of the standing first chain housing wall 40w.

A lateral rotary shaft insertion hole 41h, a second chain housing wall 41w, and a second positioning projection 41p are provided at respective predetermined positions of the flat surface 41a of the chain cover 41. The lateral rotary shaft insertion hole 41h is a through hole into which a lateral sprocket rotary shaft of the lateral sprocket 34B is inserted and disposed. A center axis (not illustrated) of the lateral rotary shaft insertion hole 41h is orthogonal to a longitudinal axis (not illustrated) of the chain cover. The second chain housing wall 41w and the second positioning projection 41p are provided at respective predetermined positions with respect to the lateral rotary shaft insertion hole 41h.

The second positioning projection 41p is a second pressing part serving as a positioning part that projects from the flat surface 41a by a height h1, as with the first positioning projection 40p. In addition, the second chain housing wall 41w is a second protrusion part serving as a protrusion that stands on the flat surface 41a by a height h2, as with the first chain housing wall 40w. The second chain housing wall 41w includes a second annular wall 41w1 and a pair of second opposing walls 41w2, as with the first chain housing wall 40w.

The second chain housing wall 40w has the height h2 that is set larger by a predetermined amount than a length of the vertical sprocket 34A in the axial direction.

A reference numeral 41S denotes a second bending operation mechanism housing chamber that includes the flat surface 40a and a second inner wall surface 41i of the second chain housing wall 41w that stands on the flat surface 40a. The vertical sprocket 34A wound with the vertical chain 35A is disposed inside the second bending operation mechanism housing chamber 41S.

The second annular wall 41$w$1 mainly constitutes a second sprocket installation space 41$ss$, prevents the vertical chain 35A wound around the vertical sprocket 34A from dropping off to the outside of the sprocket, and improves assemblability of the bending operation mechanism.

The pair of second opposing walls 41$w$2 prevents the vertical chain 35A extended from the vertical sprocket 34A, from dropping off to the outside. A space between the second opposing walls 41$w$2 is a second chain installation space space 41$sc$ that absorbs slack of the vertical chain 35A in bending operation.

The second positioning projection 41$p$ retains the vertical sprocket 34A wound with the vertical chain 35A within the second annular wall 41$w$1, in other words, prevents displacement of the vertical sprocket 34A from the second sprocket installation space 41$ss$ toward the second chain installation space space 41$sc$.

Figure 5C:
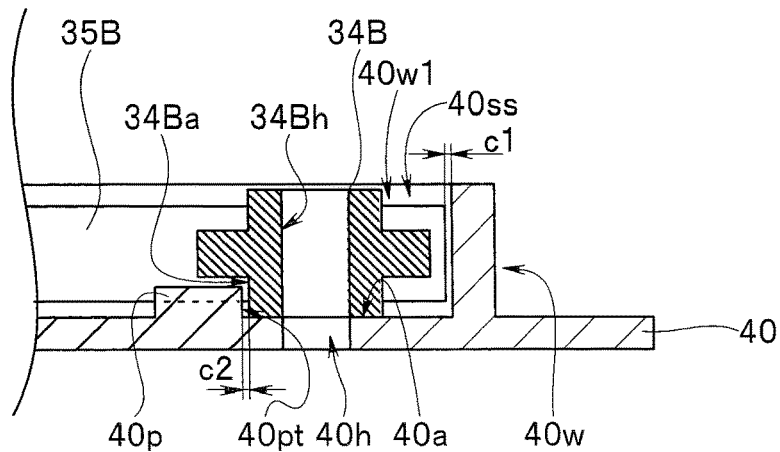
FIG. 5C is a diagram illustrating a state in which the lateral sprocket wound with the lateral chain is installed in the first sprocket installation space.
Figure 5D:
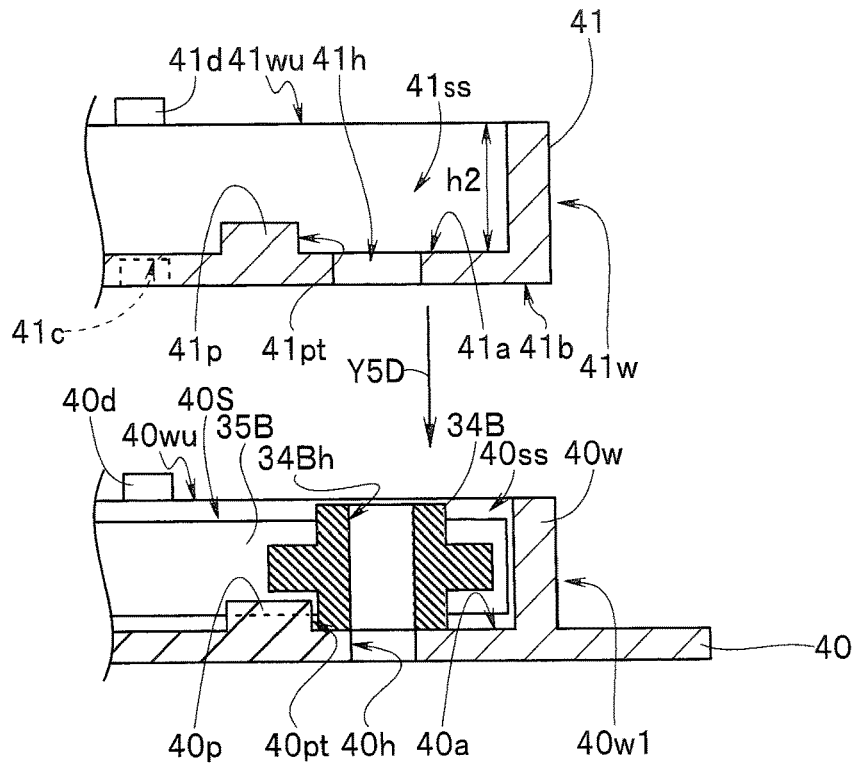
FIG. 5D is a diagram to explain a state in which a chain cover is disposed to face the main frame in which the lateral sprocket is installed in the first sprocket installation space.
Figure 5E:
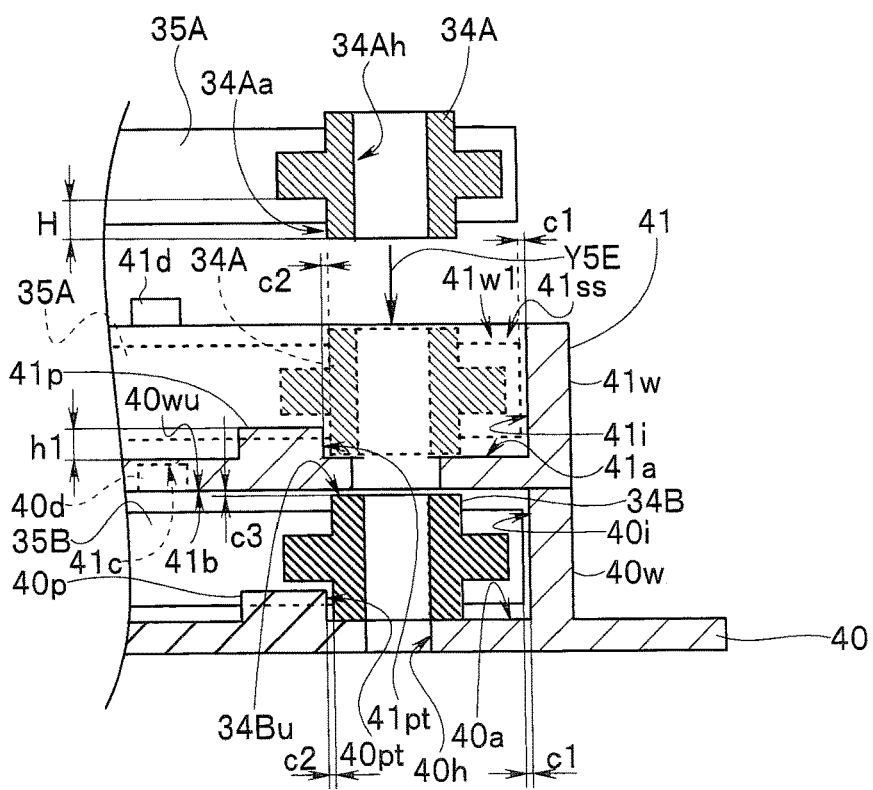
FIG. 5E is a diagram to explain a state in which the oppositely-disposed chain cover is disposed on the main frame and a state in which a vertical sprocket wound with a vertical chain is installed in a second sprocket installation space of the chain cover.

As illustrated in FIG. 5E, the second positioning projection 41$p$ has a height h1 that is set lower than a protrusion height H of the shaft part 34Aa.

In addition, as illustrated in FIG. 5E, setting is performed such that a predetermined gap c1 is provided between the second inner wall surface 41$i$ of the second annular wall 41$w$1 and the outer side of the vertical chain 35A wound around the vertical sprocket 34A. Further, the setting is performed such that a predetermined gap c2 is provided between the contact surface 41$pt$ of the second positioning projection 41$p$ and an outer peripheral surface of the shaft part 34Aa serving as a contact part.

A reference numeral 41$d$ in FIG. 4 denotes a second attachment dowel. The second attachment dowel 41$d$ is provided at a predetermined position on end part side of each of the second opposing walls 41$w$2 and projects from a top surface of the end part by a predetermined amount.

The lid member 42 is a third plate member, and includes a flat surface 42$a$ and the other flat surface 42$b$ that is a surface opposite to the flat surface 42$a$. The other flat surface 42$b$ is a surface disposed to face the flat surface 41$a$ of the chain cover 41, and is disposed on an end surface of the standing second chain housing wall 41$w$.

A vertical rotary shaft insertion hole 42$h$1 is provided at a predetermined position of the lid member 42. The vertical rotary shaft insertion hole 42$h$1 is a through hole into which a vertical sprocket rotary shaft of the vertical sprocket 34A is inserted and disposed. A center axis (not illustrated) of the vertical rotary shaft insertion hole 42$h$1 is orthogonal to a longitudinal axis (not illustrated) of the lid member.

A reference numeral 42$h$2 denotes an attachment dowel engagement hole that is a through hole. Paired attachment dowels 41$d$ projected from the second opposing walls 41$w$2 respectively engage with paired attachment dowel engagement holes 42$h$2.

Note that various kinds of tube pipes and metal tubes that constitute the video cable, the light guide fiber, the air feeding conduit, and the water feeding conduit are installed on the unillustrated other surface side of the main frame 40 illustrated in FIG. 3.

A procedure of assembling the bending operation mechanism 30 to the flat surface 40$a$ of the main frame 40 is described here.

First, an operator winds a middle part of the lateral chain 35B around the lateral sprocket 34B. Thereafter, the operator disposes the lateral sprocket 34B wound with the lateral chain 35B such that the lateral sprocket 34B faces the flat surface 40$a$ of the main frame 40, as illustrated in FIG. 5A.

Next, the operator disposes the lateral sprocket 34B wound with the lateral chain 35B, inside the first sprocket installation space 40$ss$. At the time, the operator holds, by a thumb and a finger other than the thumb, the lateral sprocket 34B through the lateral chain 35B, and moves the lateral sprocket 34B toward the flat surface 40$a$ as illustrated by an arrow Y5A while bringing the outer side of the lateral chain 35B wound around the lateral sprocket 34B close to the first inner wall surface 40$i$ of the first annular wall 40$w$1 in the holding state.

Then, as illustrated in FIG. 5B, the operator disposes the distal end surface side of the lateral shaft part 34Ba of the lateral sprocket 34B near the contact surface 40$pt$ of the first positioning projection 40$p$. At this time, the operator further moves the lateral shaft part 34Ba toward the flat surface 40$a$ as illustrated by an arrow Y5B while bringing the outer side of the lateral chain 35B into contact with the first inner wall surface 40$i$ of the first annular wall 40$w$1.

As a result, as illustrated in FIG. 5C, the lateral shaft part 34Ba of the lateral sprocket 34B wound with the lateral chain 35B is installed inside the first sprocket installation space 40$ss$ while being placed on the flat surface 40$a$.

In the installation state, the outer side of the lateral chain 35B wound around the lateral sprocket 34B is so disposed as to form a predetermined clearance with respect to the first inner wall surface 40$i$ of the first annular wall 40$w$1, and the outer peripheral surface on the distal end side of the lateral shaft part 34Ba is so disposed as to form a predetermined clearance with respect to the contact surface 40$pt$ of the first positioning projection 40$p$.

Accordingly, the lateral sprocket 34B is rotatably disposed inside the first sprocket installation space 40$ss$. In addition, the lateral sprocket 34B is disposed such that the center axis of a shaft insertion hole 34Bh of the lateral sprocket 34B is coincident with the center axis of the support shaft hole 40$h$.

Next, the operator disposes the lateral rotary shaft insertion hole 41$h$ provided in the chain cover 41 such that the lateral rotary shaft insertion hole 41$h$ faces the distal end portion of the unillustrated lateral sprocket rotary shaft, as illustrated in FIG. 5D. Then, the operator moves the chain cover 41 as illustrated by an arrow Y5D to bring the other flat surface 41$b$ of the chain cover 41 close to a top surface 40$wu$ of the first chain housing wall 40$w$.

Figure 5F:
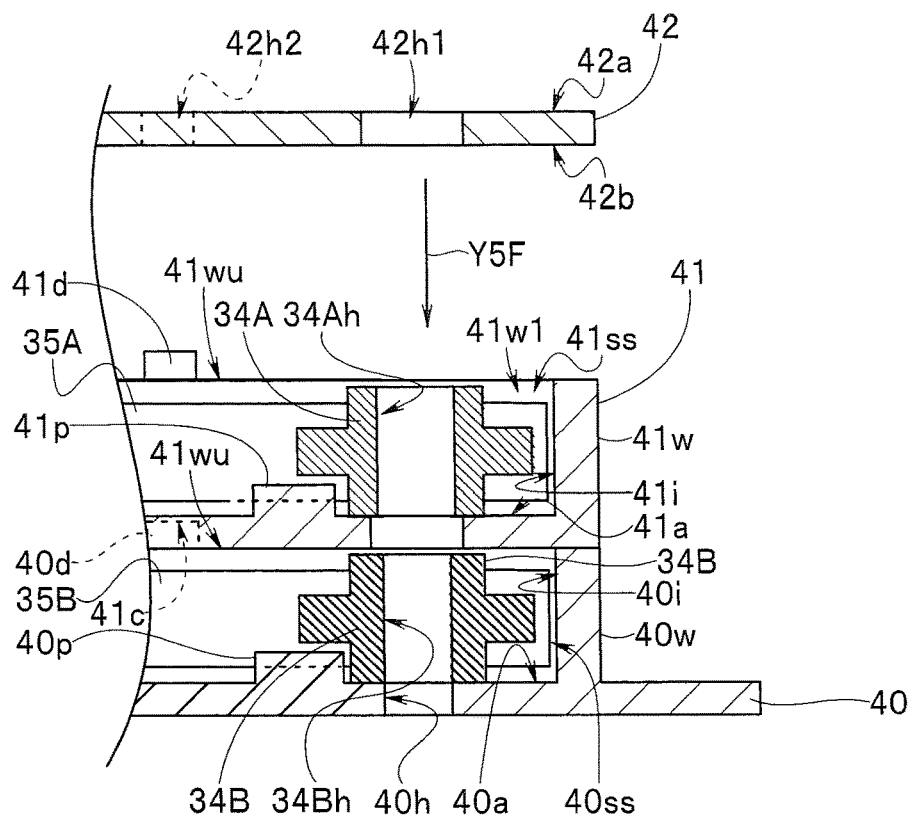
FIG. 5F is a diagram to explain the chain cover and a lid member that are disposed on the main frame.

Then, the operator causes the paired attachment holes 41$c$ as concave parts to respectively engage with the paired attachment dowels 40$d$, as illustrated in FIG. 5F. As a result, the chain cover 41 is installed on the top surface 40$wu$ of the first chain housing wall 40$w$ of the main frame 40 without a fixing screw.

Note that, in the state in which the chain cover 41 is installed, a desired clearance c3 is provided between the other flat surface 41$b$ of the chain cover 41 and a top surface 34Bu of the lateral sprocket 34B. As a result, the lateral sprocket 34B is rotatable in the state in which the chain cover 41 is placed on the main frame 40.

After the chain cover 41 is installed, the operator disposes the vertical sprocket 34A wound with the vertical chain 35A, in the second sprocket installation space 41$ss$ of the chain cover 41, as illustrated in FIG. 5E. At this time, the operator holds, by the thumb and a finger other than the thumb, the vertical sprocket 34A through the vertical chain 35A, and moves the vertical sprocket 34A toward the flat surface 41$a$ of the chain cover 41 as illustrated by an arrow Y5E in FIG. 5E.

At this time, the outer side of the vertical chain 35A wound around the vertical sprocket 34A is brought close to the second inner wall surface 41$i$ of the second annular wall 41$w$1, and is moved toward the flat surface 41$a$.

Then, the distal end surface side of the vertical shaft part 34Aa of the vertical sprocket 34A is disposed near the contact surface 41pt of the second positioning projection 41p. At this time, the operator moves the vertical sprocket 34A toward the flat surface 41a.

As a result, the vertical shaft part 34Aa of the vertical sprocket 34A wound with the vertical chain 35A is installed in the second sprocket installation space 41ss while being placed on the flat surface 41a, as illustrated by a dashed line in FIG. 5E.

In the installation state, the outer side of the vertical chain 35A is so disposed as to form a predetermined clearance with respect to the first inner wall surface 40i of the second annular wall 41w1, and the outer peripheral surface on the distal end side of the vertical shaft part 34Aa is so disposed as to form a predetermined clearance with respect to the contact surface 41pt of the second positioning projection 41p.

Accordingly, the vertical sprocket 34A is rotatable around the lateral sprocket rotary shaft inside the second sprocket installation space 41ss.

Note that, in the above-described installation work, the chain cover 41 is placed on the main frame 40. Therefore, the lateral sprocket 34B wound with the lateral chain 35B is rotatably disposed without dropping from the first sprocket installation space 40ss and without moving inside the first sprocket installation space 40ss.

In addition, in the above-described embodiment, the outer side of the chains 35A and 35B are so disposed as to form a predetermined clearance with respect to the first inner wall surface 40i, and the outer peripheral surfaces on the distal end side of the shaft parts 34Aa and 34Ba are so disposed as to form a predetermined clearance with respect to the contact surfaces 41pt and 40pt of the positioning projections 41p and 40p, respectively. In a configuration in which a wire wound around an unillustrated pulley is so disposed as to form a predetermined clearance with respect to a first inner wall surface of an unillustrated pulley installation space, however, the outer peripheral surfaces on the distal end side of the shaft parts 34Aa and 34Ba may not desirably form a clearance with respect to the contact surfaces 41pt and 40pt of the positioning projections 41p and 40p, respectively.

Figure 5G:
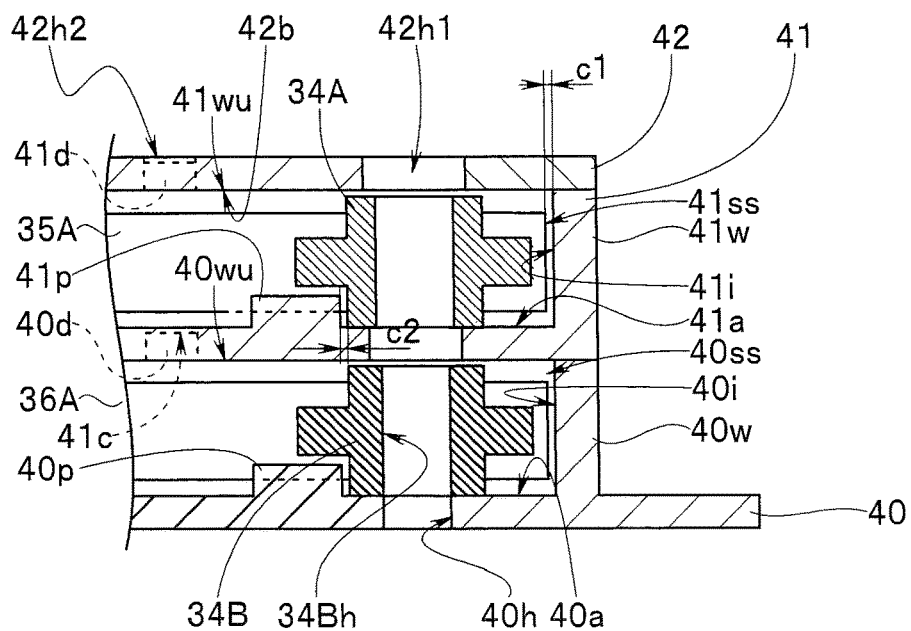
FIG. 5G is a diagram to explain a state in which the lid member is disposed on the chain cover.

Next, the operator brings the other flat surface 42b of the lid member 42 close to the top surface 41wu of the second chain housing wall 41w, as illustrated by an arrow 5F in FIG. 5F. Then, the operator causes the paired attachment holes 42h2 to engage with the paired second attachment dowels 41d, as illustrated in FIG. 5G. As a result, the lid member 42 is installed on the top surface 41wu of the second chain housing wall 41w of the chain cover 41 without a fixing screw.

Figure 5H:
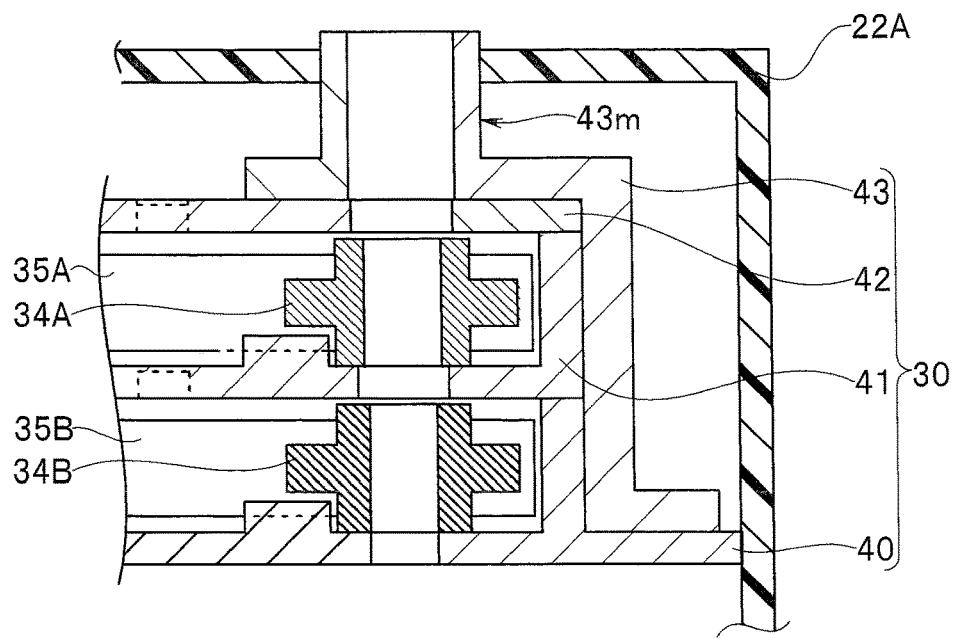
FIG. 5H is a diagram to explain a state in which the main frame provided with the lateral sprocket, the lateral chain, the vertical sprocket, and the vertical chain is fixed to an operation section body to which a frame shaft is assembled.

Next, the operator assembles the frame shaft 43 to the operation section body 22A. Thereafter, as illustrated in FIG. 5H, the operator fixes the main frame 40 to the operation section body 22A to which the frame shaft 43 has been assembled, by unillustrated screws in a predetermined state. At this time, in the work of inserting the main frame 40 into the frame shaft 43, it is necessary for the operator to insert the main frame 40 while performing visual confirmation because the member group on the main frame 40 has a shape substantially same as the inner shape of the frame shaft 43. To perform visual confirmation, it is necessary for the operator to look into the inside of the frame shaft 43 covered with the operation section body 22A, from an operation section body cover 22Ac side described later. Therefore, the operator may incline or invert the components under assembly.

As a result, the bending operation mechanism 30 that is configured by sequentially assembling the chain cover 41, the lid member 42, and the frame shaft 43 to the main frame 40, is provided to the operation section body 22A.

Figure 5I:
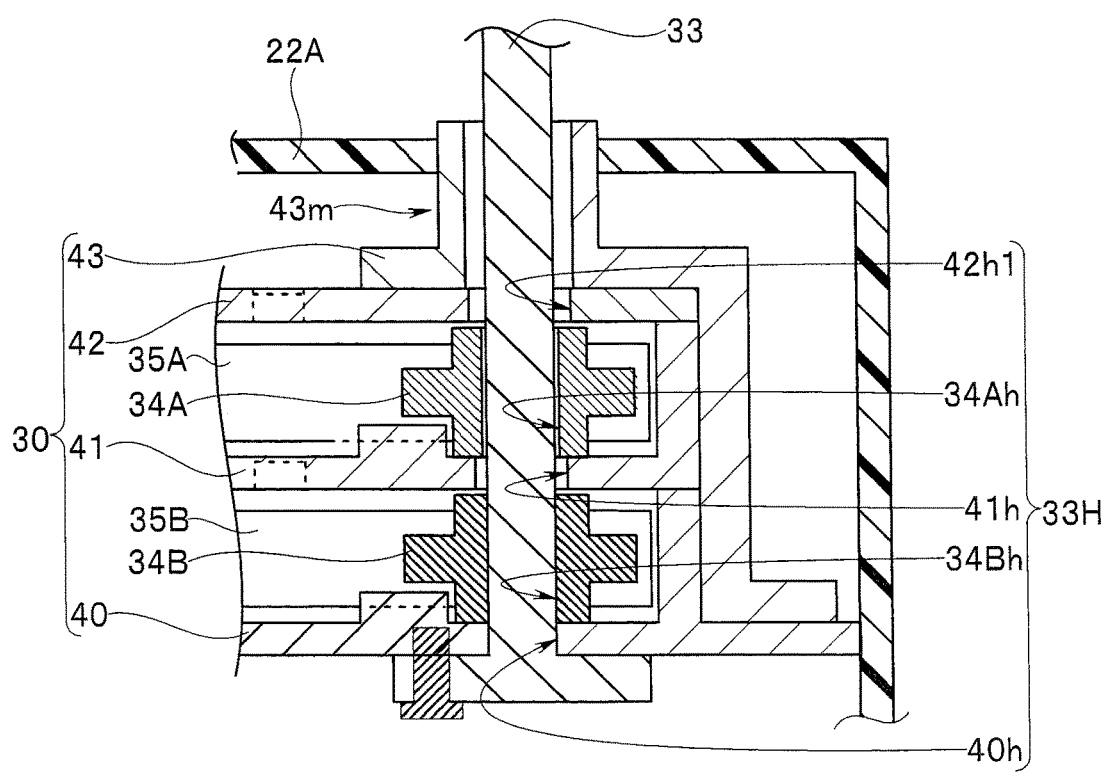
FIG. 5I is a diagram illustrating a state in which a support shaft is inserted into a support shaft insertion hole.

The operator inserts the support shaft 33 into a support shaft insertion hole 33H as illustrated in FIG. 5I. The support shaft insertion hole 33H includes a support shaft hole 40h, a vertical sprocket insertion hole 34Ah, a lateral sprocket insertion hole 34Bh, a lateral rotary shaft insertion hole 41h, and a vertical rotary shaft insertion hole 42h1.

The vertical sprocket 34A and the vertical chain 35A are positioned by the second positioning projection 41p and the inner wall surface 41i, and the lateral sprocket 34B and the lateral chain 35B are positioned by the first positioning projection 40p and the inner wall surface 40i.

Accordingly, a center axis of the vertical sprocket insertion hole 34Ah and a center axis of the lateral sprocket insertion hole 34Bh are so disposed as to be coaxial with a center axis of the support shaft insertion hole 40h, a center axis of the lateral rotary shaft insertion hole 41h, and a center axis of the vertical rotary shaft insertion hole 42h1.

Next, the operator assembles a vertical sprocket rotary shaft 31Aa and a lateral sprocket rotary shaft 31Ba to the operation section 22. The vertical sprocket rotary shaft 31Aa is configured integrally with the vertical bending operation knob 31A, and the lateral sprocket rotary shaft 31Ba is configured integrally with the lateral bending operation knob 31B.

Figure 5J:
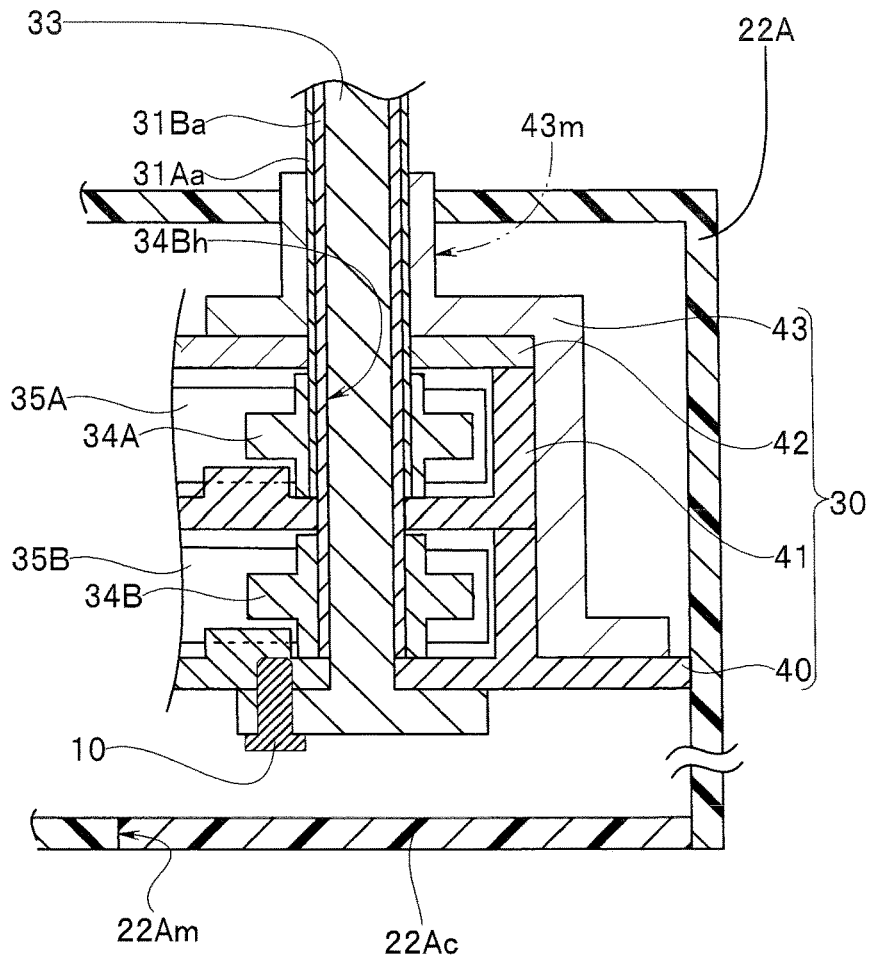
FIG. 5J is a cross-sectional diagram taken along line Y5J-Y5J in FIG. 3, illustrating the bending operation mechanism of the operation section.

Further, the operator installs, in the operation section 22, various kinds of tube pipes and the like that constitute a video cable, a light guide fiber, an air feeding conduit, and a water feeding conduit not illustrated. The operator then assembles the operation section body cover 22Ac to the opening 22Am that is provided in the operation section body 22A, as illustrated in FIG. 5J. As a result, the bending operation mechanism 30 is installed inside the operation section 33.

As mentioned above, it is necessary for the operator to incline or invert the components under assembly, in the work of inserting the main frame 40 into the frame shaft 43. This may make displacement of the center axis of the vertical sprocket insertion hole 34Ah, the center axis of the lateral sprocket insertion hole 34Bh, the center axis of the support shaft insertion hole 40h, the center axis of the lateral rotary shaft insertion hole 41h, and the center axis of the vertical rotary shaft insertion hole 42h1 easy to occur. However, when the vertical sprocket 34A and the vertical chain 35A are positioned by the second positioning projection 41p and the inner wall surface 41i, the lateral sprocket 34B and the lateral chain 35B are positioned by the first positioning projection 40p and the inner wall surface 40i, and the center axis of the vertical sprocket insertion hole 34Ah and the center axis of the lateral sprocket insertion hole 34Bh are so disposed as to be coaxial with the center axis of the support shaft insertion hole 40h, the center axis of the lateral rotary shaft insertion hole 41h, and the center axis of the vertical rotary shaft insertion hole 42h1, it is possible to improve assemblability in insertion of the support shaft 33 into the support shaft insertion hole 33H that includes the support shaft hole 40h, the vertical sprocket insertion hole 34Ah, the lateral sprocket insertion hole 34Bh, the lateral rotary shaft insertion hole 41h, and the vertical rotary shaft insertion hole 42h1.

Figure 6:
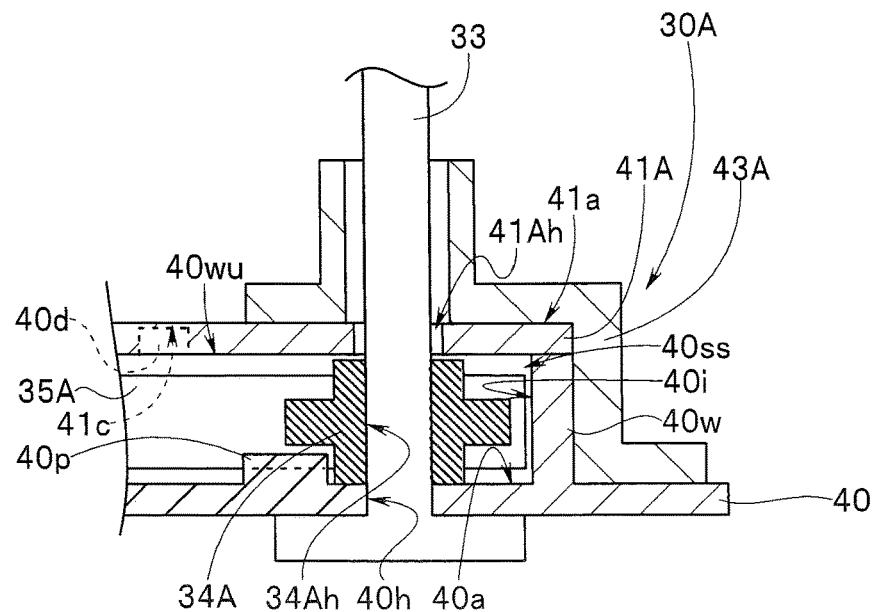
FIG. 6 is a diagram to explain the bending operation mechanism for a configuration in which a bending portion of the endoscope is bent in two directions of upward and downward.

Note that, in the above-described endoscope 20, the bending portion 21b is bendable in four directions of upward, downward, rightward, and leftward. The bending portion of the endoscope, however, may be bendable in two directions of upward and downward, or the like. In such a case, a bending operation mechanism 30A illustrated in FIG. 6 is configured.

The bending operation mechanism 30A includes the main frame 40, the vertical chain 35A, the vertical sprocket 34A, a chain cover 41A, and a frame shaft 43A.

In the present embodiment, a vertical rotary shaft insertion hole 41Ah is provided in the flat surface 41a of the chain cover 41A, and the second chain housing wall 41w, the second positioning projection 41p, and the second attachment dowels 41d are not provided. In other words, the chain cover 41A has a configuration substantially similar to the configuration of the lid member 42.

Further, the main frame 40 and the chain cover 41 may be configured in the following manner, in consideration of workability.

Figure 7A:
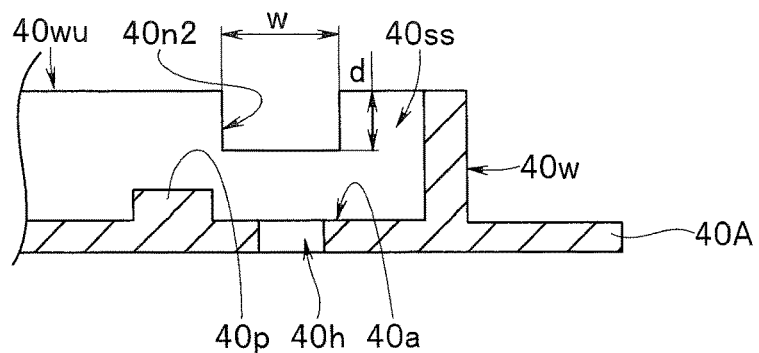
FIG. 7A is a cross-sectional diagram, in a longitudinal direction, of a main frame including a pair of cutout grooves.
Figure 7B:
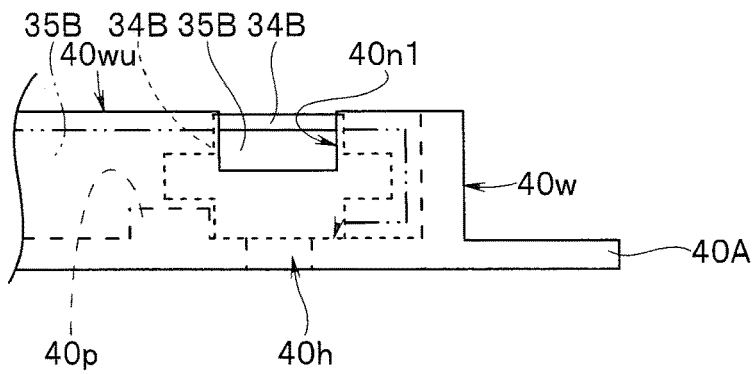
FIG. 7B is a side view of the main frame including the pair of cutout grooves.
Figure 7C:
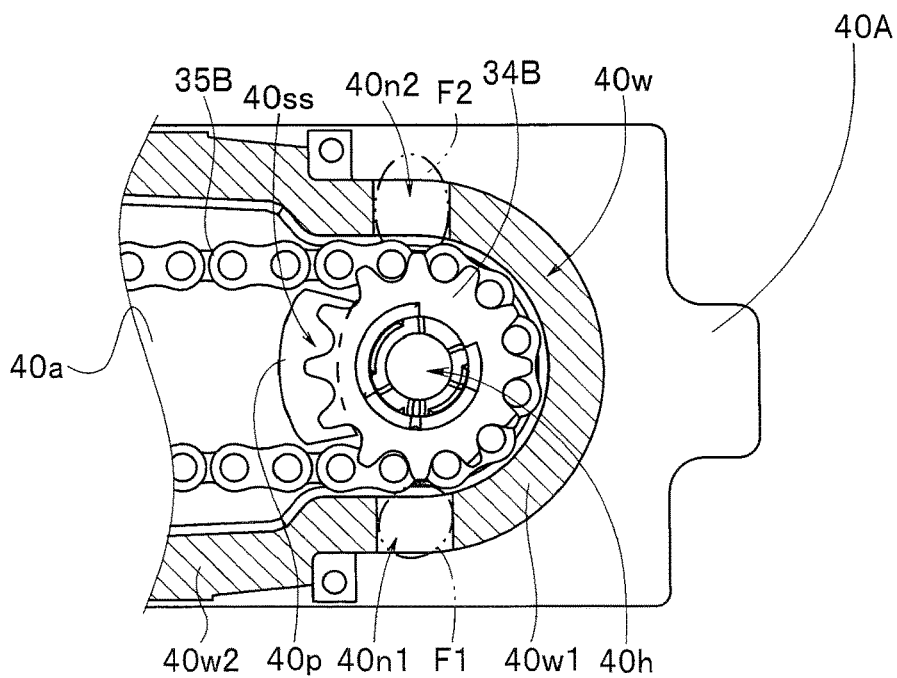
FIG. 7C is a diagram to explain a state in which the main frame including the pair of cutout grooves and the lateral sprocket wound with the lateral chain are held by fingers.

As illustrated in FIG. 7A, FIG. 7B, and FIG. 7C, for example, two cutout grooves 40n1 and 40n2 are provided near a boundary between the first annular wall 40w1 and each of the first opposing walls 40w2 of the chain housing wall 40w provided in a main frame 40A. The cutout grooves 40n1 and 40n2 serve as cutout parts facing each other with the center axis of the support shaft hole 40h in between.

A width w of each of the cutout grooves 40n1 and 40n2 is set to cause a tip of a thumb F1 and a tip of a finger F2 other than the thumb that hold the lateral sprocket 34B through the lateral chain 35B, to be located inside the first sprocket installation space 40ss. A depth d of each of the cutout grooves 40n1 and 40n2 from the top surface 40wu of the first chain housing wall 40w is set to allow a shaft end surface of the lateral sprocket 34B wound with the lateral chain 35B to be smoothly disposed on the flat surface 40a that is a bottom surface of the first sprocket installation space 40ss.

When the operator holds, by a thumb and, for example, a middle finger, the lateral sprocket 34B through the lateral chain 35B to install the lateral sprocket 34B into the first sprocket installation space 40ss, the above-described configuration allows the operator to dispose the thumb and the middle finger holding the lateral sprocket 34B on the top surface 40wu of the first chain housing wall 40w. Then, the operator moves the thumb toward the flat surface 40a along the first cutout groove 40n1 and moves the middle finger toward the flat surface 40a along the second cutout groove 40n2, thereby performing the installation.

As a result, when the lateral sprocket 34B wound with the lateral chain 35B is disposed inside the first sprocket installation space 40ss, it is possible to smoothly perform the installation work without inhibiting the movement by the top surface 40wu of the first chain housing wall 40w and without detachment of the lateral chain 35B from the lateral sprocket 34B.

Note that the configuration in which the cutout grooves 40n1 and 40n2 are provided in the main frame 40 is illustrated with reference to FIG. 7A to FIG. 7C; however, cutout parts 41n1 and 41n2 each having a configuration similar to the above-described configuration may be provided in the chain cover 41.

Such a configuration makes it possible to smoothly perform the installation work without inhibiting movement by the top surface 41wu of the second chain housing wall 41w and without detachment of the vertical chain 35A from the vertical sprocket 34A, when the vertical sprocket 34A wound with the vertical chain 35A is installed inside the second sprocket installation space 41ss.

Figure 8A:
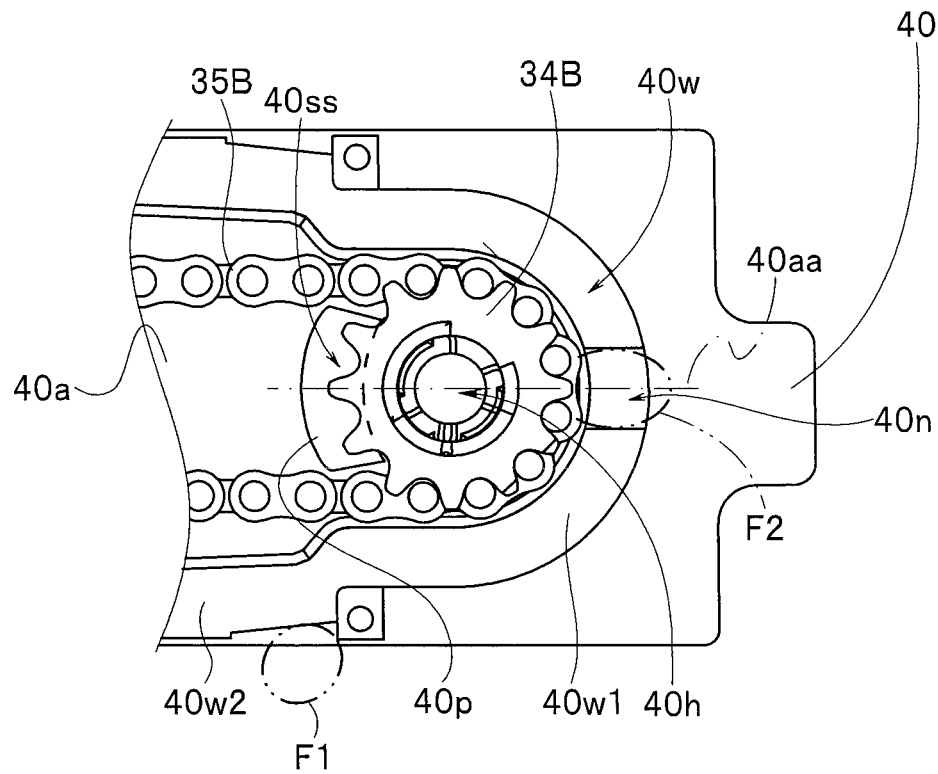
FIG. 8A is a diagram to explain a state in which a main frame including one cutout groove and the lateral sprocket wound with the lateral chain are held by fingers.
Figure 8B:
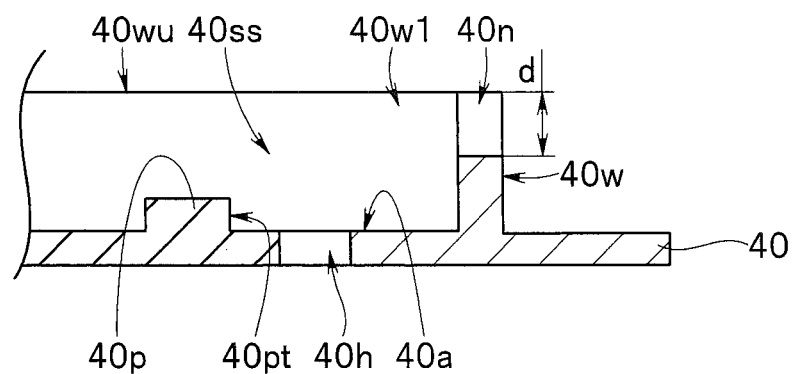
FIG. 8B is a cross-sectional diagram, in a longitudinal direction, of the main frame including one cutout groove.

In addition, in the above-described embodiment, the two cutout grooves 40n1 and 40n2 are so provided near the respective boundaries between the first annular wall 40w1 and each of the first opposing walls 40w2, as to face each other with the center axis of the support shaft hole 40h in between. The cutout parts, however, are not limited to the paired cutout parts facing each other, and only one cutout groove 40n on which the tip of the thumb F1 or the tip of the finger F2 other than the thumb is disposed may be provided on an apex of an annular wall that intersects with a longitudinal axis 40aa, as illustrated in FIG. 8A and FIG. 8B. The longitudinal axis 40aa passes through the center of the support shaft hole 40h of the annular wall 40w1.

In the case of the configuration, the operator holds, for example, by the thumb and a forefinger, the sprocket through the chain, and disposes the thumb and the forefinger on the top surface 41wu of the annular wall 40w1 in the holding state. Then, the operator moves one of the fingers, for example, the forefinger toward the flat surface 40a along the cutout groove 40n. As a result, it is possible for the operator to smoothly and surely install the sprocket wound with the chain in the first sprocket installation space 40ss, as with the above description.

Note that the cutout groove 41n having a configuration similar to the above-described configuration may be provided in the chain cover 41.

Figure 9:
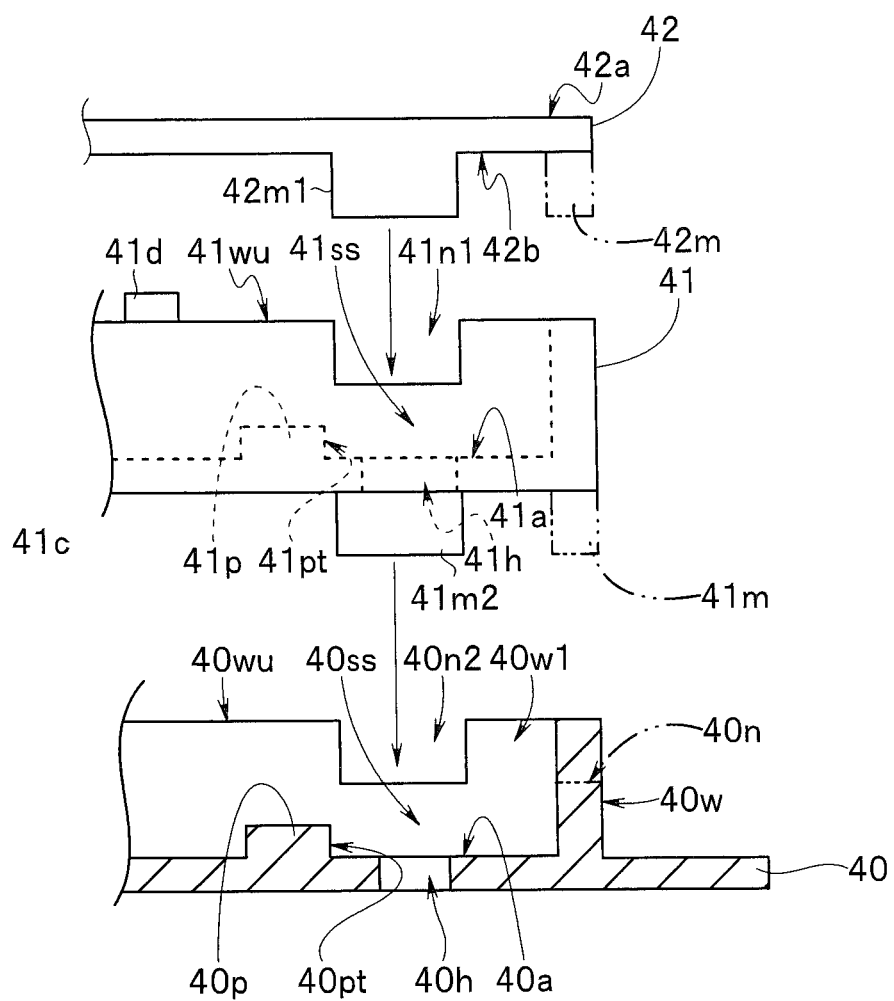
FIG. 9 is a diagram to explain a chain cover and a lid member each including a complementary part corresponding to the cutout groove.

In addition, as mentioned above, a complementary part is provided in each of the chain cover 41 and the lid member 42 as illustrated in FIG. 9, in the configuration in which the cutout grooves 40n, 40n1, and 40n2 are provided in the main frame 40 and in the configuration in which the cutout grooves 41n, 41n1, and 41n2 are provided in the chain cover 41.

A complementary part 41m provided in the chain cover 41 is disposed inside the cutout groove 40n of the main frame 40, and a complementary part 41m1 is disposed inside the cutout groove 40n1 of the main frame 40, and a complementary part 41m2 is disposed inside the cutout groove 40n2 of the main frame 40.

In contrast, a complementary part 42m provided in the lid member 42 is disposed inside the cutout groove 41n of the chain cover 41, a complementary part 41m1 is disposed inside the cutout groove 41n1 of the chain cover 41, and a complementary part 41m2 is disposed in the cutout groove 41n2 of the chain cover 41.

The complementary parts 41m, . . . , 42m, 42m2 are so disposed inside the respective cutout grooves 40n, . . . , 41n, . . . , 41n2 as to bury the respective cutout grooves 40n, . . . , 41n, . . . , 41n2. In the state in which the complementary parts 41m, . . . , 42m, . . . , 42m2 are respectively disposed inside the cutout grooves 40n, . . . , 41n, . . . , 41n2, the lateral chain 35B is disposed inside the first sprocket installation space 40ss that has a shape similar to the shape of the above-described embodiment, which results in action and effects similar to the action and effects of the above-described embodiment. The vertical chain 35A is also disposed inside the second sprocket installation space 41ss that has a shape similar to the shape of the above-described embodiment, which results in action and effects similar to the action and effects of the above-described embodiment.

Further, the configuration allows for manufacturing of the chain cover with use of a material such as polyacetal, thereby improving operability of the endoscope. The chain cover made of the material having excellent slipperiness such as polyacetal has improved slipperiness with the sprocket or the chain to be contacted. Improvement of the slipperiness between the components may typically cause deterioration of assembling work; however, the configuration does not influence the assembling work even when the slipperiness between the components is improved, and it is possible to reduce an amount of operation force of the endoscope operator, and to improve operability of the endoscope. Accordingly, improvement of both operability and assemblability of the endoscope is realizable.

In the present embodiment, the positioning projection 40p and the chain housing wall 40w for disposing of the lateral sprocket 34B are provided in the main frame 40; however, the positioning projection and the chain housing wall for disposing of the lateral sprocket 34B may be provided in the chain cover 41.

In a modification of the embodiment, the vertical chain 35A, the vertical sprocket 34A, the positioning projection 41p and the chain housing wall 41w are disposed on a front surface as a first surface of the chain cover 41. Further, the lateral chain 35B, the lateral sprocket 34B, an unillustrated positioning projection, and an unillustrated chain housing wall are disposed on a rear surface as a second surface of the chain cover 41.

The vertical chain 35A is a chain that is pulled to bend the bending portion 21b in the vertical direction.

The vertical sprocket 34A includes the tooth part 34Ac and the vertical shaft part 34Aa. The tooth part 34Ac engages with the vertical chain 35A as a traction member, and the vertical shaft part 34Aa fixes the tooth part 34Ac. The vertical sprocket 34A causes the vertical chain 35A to engage with the tooth part 34Ac to wind the vertical chain 35A, and rotates to pull the vertical chain 35A.

The chain housing wall 41w is a protrusion to position the vertical sprocket 34A and the vertical chain 35A with respect to the chain cover 41. The chain housing wall 41w protrudes from the surface of the chain cover 41.

The positioning projection 41p is a positioning part to position the vertical sprocket 34A. The positioning projection 41p so protrudes from the surface of the chain cover 41 as to come into contact with the vertical shaft part 34Aa of the vertical sprocket 34A.

The lateral chain 35B is a chain that is pulled to bend the bending portion 21b in the lateral direction.

The lateral sprocket 34B has the tooth part 34Bc and the lateral shaft part 34Ba. The tooth part 34Bc engages with the lateral chain 35B as a traction member, and the lateral shaft part 34Ba fixes the tooth part 34Bc. The lateral sprocket 34B causes the lateral chain 35B to engage with the tooth part 34Bc to wind the lateral chain 35B, and rotates to pull the lateral chain 35B.

The unillustrated chain housing wall for disposing of the lateral chain 35B is a protrusion to position the lateral sprocket 34B and the lateral chain 35B with respect to the chain cover 41. The chain housing wall protrudes from the rear surface of the chain cover 41.

The unillustrated positioning projection for disposing of the lateral chain 35B is a positioning part to position the lateral sprocket 34. The positioning projection so protrudes from the rear surface of the chain cover 41 as to come into contact with the lateral shaft part 34Ba of the lateral sprocket 34B.

The above-described modification of the embodiment makes it possible to realize the endoscope that is excellent in assemblability and prevents the traction member wound around the rotary member from being detached from the rotary member while positioning the installation position of the rotary member on the front surface and the rear surface of the chain cover 41.

The present invention makes it possible to realize the endoscope that is excellent in assemblability and prevents the traction member wound around the rotary member from being detached from the rotary member while positioning the installation position of the rotary member on the flat surface of the plate member.

Note that the present invention is not limited to the above-described embodiment, and may be variously modified without departing from the scope of the invention.

What is claimed is:

1. An endoscope comprising:
   a bendable bending portion provided in an insertion section that is inserted into a subject;
   a first traction member and a second traction member that are pulled to bend the bending portion;
   a first rotary member including a first engaging part that engages with the first traction member, a first shaft part that fixes the first engaging part, and a first insertion hole that penetrates in an axial direction of the first shaft part, the first rotary member causing the first traction member to engage with the first engaging part to wind the first traction member, and rotating to pull the first traction member;
   a first plate member on which the first rotary member and the first traction member are disposed, the first plate member being formed in a plate shape;
   a first protrusion protruding from the first plate member to position the first rotary member and the first traction member with respect to the first plate member;
   a first positioning part protruding from the first plate member to position the first rotary member, and coming into contact with the first shaft part of the first rotary member;
   a second rotary member including a second engaging part that engages with the second traction member, a second shaft part that fixes the second engaging part, and a second insertion hole that penetrates in an axial direction of the second shaft part, the second rotary member causing the second traction member to engage with the second engaging part to wind the second traction member, and rotating to pull the second traction member;
   a second plate member that is a plate member including a first surface disposed on an end surface of the first protrusion and a second surface on which the second rotary member and the second traction member are disposed, the second surface being a rear surface side of the first surface, the second plate member including a third insertion hole that penetrates the first surface and second surface such that the third insertion hole has a common axis with the first insertion hole and the first rotary member and the second rotary member rotate about the common axis;
   a second protrusion protruding from the second plate member to position the second rotary member and the second traction member with respect to the second plate member; and
   a second positioning part protruding from the second plate member to position the second insertion hole so as to be coaxial with the third insertion hole, the second positioning part coming into contact with the second shaft part of the second rotary member.

2. The endoscope according to claim 1, wherein the first protrusion is formed integrally with and protruded from the first plate member, and the second protrusion is formed integrally with and protruded from the second plate member.

3. The endoscope according to claim 1, wherein
   the first positioning part includes a first pressing part protruding from the first plate member to position the first rotary member with respect to the first plate member and coming into contact with the first shaft part of the first rotary member, and the second positioning part includes a second pressing part protruding from the second plate member to position the second rotary member with respect to the second plate member and coming into contact with the second shaft part of the second rotary member.

* * * * *